United States Patent [19]

Swithenbank et al.

[11] Patent Number: 4,877,897
[45] Date of Patent: Oct. 31, 1989

[54] 4-TRIFLUOROMETHYL-4'-NITRODIPHENYL ETHERS

[75] Inventors: Colin Swithenbank, Perkasie; Ted. T. Fujimoto, Churchville, both of Pa.

[73] Assignee: Rohm and Haas Company, Philadelphia, Pa.

[21] Appl. No.: 440,700

[22] Filed: Nov. 10, 1982

Related U.S. Application Data

[60] Division of Ser. No. 386,455, Jun. 8, 1982, which is a continuation of Ser. No. 149,618, May 14, 1980, abandoned, which is a continuation-in-part of Ser. No. 47,654, Jun. 11, 1979, abandoned.

[51] Int. Cl.$^4$ .............................................. C07C 79/46
[52] U.S. Cl. ...................................... 560/021; 71/111
[58] Field of Search ............................................ 560/21

[56] References Cited

U.S. PATENT DOCUMENTS 3,282,991 11/1966 Klein et al. .................... 260/501
4,063,929 12/1977 Bayer et al. ..................... 71/115

FOREIGN PATENT DOCUMENTS 0013660 7/1980 European Pat. Off. .............. 560/21

OTHER PUBLICATIONS

*Organic Chemistry,* Sixth Edition, Barnes and Noble, Inc., New York pp. 87–93 and 136–138.
*Pesticides in Soil and Water,* Soil Science Society of America, Inc., Wisconsin (1974), pp. 123 and 128.
*Herbicides,* Second Edition, vol. 2, Academic Press, London, (1976), pp. 29 and 47–49.
*Herbicides,* Second Edition, Revised and Expanded, vol., 2, Marcel Dekker, Inc. New York, (1976), pp. 709, 724–725.
*Herbicides,* Second Edition, vol. 2, Academic Press, London, (1976), pp. 65, 72, 91, 92.
*Pesticides in Soil and Water,* Soil Science of America, Inc., Wisconsin, (1974), pp. 203–207, 218–222.
*Organic Compounds in Soils: Sorption, Degradation and Persistance,* Ann Arbor Science, Michigan, (1982), p. 242.
*Herbicide Handbook of the Weed Science Society of America,* 5th Edition, (1983), pp. 54–59.

*Primary Examiner*—Paul J. Killos
*Attorney, Agent, or Firm*—T. P. Strobaugh

[57] ABSTRACT

Compounds of the formula:

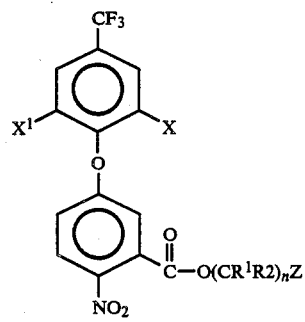

wherein X is hydrogen, halo, trihalomethyl, alkyl, nitro or cyano; $X^1$ is hydrogen, halo, or trihalomethyl; $R^1$ and $R^2$ are hydrogen, alkyl, phenyl or benzyl; n is 1 to 5, and Z is nitro, and compositions containing these compounds exhibit herbicidal activity.

11 Claims, No Drawings

4-TRIFLUOROMETHYL-4'-NITRODIPHENYL ETHERS

THE DISCLOSURE

This is a division of Ser. No. 386,455 filed June 8, 1982 which is a continuation of Serial No. 149,618 filed May 14, 1980, now abandoned which was a continuation-in-part of Ser. No. 047,654 filed June 11, 1979 now abandoned.

This invention relates to 4-trifluoromethyl-4'-nitrodiphenyl ethers, compositions containing a 4-trifluoromethyl-4'-nitrodiphenyl ether and to methods of controlling weeds.

Diphenyl ethers are known to be effective weed control agents. See for example U.S. Pat. Nos. 3,928,416; 3,454,392; 3,798,276; 3,873,303; 4,001,005; and 4,029,493 among the many patents issued. However, even now herbicidal effectiveness of a diphenyl ether cannot be predicted known only the structures. Often, quite closely related compounds will have quite different weed control abilities. See, *Advances in Agronomy*, Vol. 24, pages 331, 332, 355, 356, 357 and 358, *Herbicides, Chemical Degradation and Mode of Action*, Kearney and Kaufman, Vol. 2, Dekker, Inc. pages 552–563 and 728–737 and *Mode of Action of Herbicides*, Ashton and Crafts and also U.S. Pat. Nos. 3,454,392 and 3,776,961.

An ideal herbicide should give selective weed control, over the full growing season, with a single administration at low rates of application. It should be able to control all common weeds by killing them as the seed, the germinating seed, the seedling, and the growing plant. At the same time, the herbicide should be substantially non-phytotoxic to the crops to which it is applied and should decompose or otherwise be dissipated so as not to poison the soil permanently. The known diphenyl ether herbicides fall short of these ideals and thus the search continues to discover new herbicides which are more selective or which complement the known diphenyl ethers and other herbicides.

In accordance with the present invention, there is provided a new class of diphenyl ether herbicides having the following structural formula:

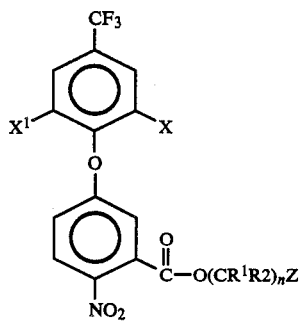

wherein X is hydrogen, halo, for example, bromo, chloro, fluoro, iodo and the like, trihalomethyl, for example, trifluoromethyl and the like, alkyl, for example, lower alkyl of from 1 to 4 carbon atoms such as methyl, ethyl, n-propyl, n-butyl, tert-butyl and the like; nitro, or cyano; $X^1$ is hydrogen, halo, for example, bromo, chloro, fluoro, iodo and the like, or trihalomethyl, such as trifluoromethyl and the like; $R^1$ and $R^2$ are the same or different radicals selected from hydrogen, lower alkyl of from 1 to 4 carbon atoms, phenyl or benzyl; n is an integer of from 1 to 5 and Z is nitro. In a preferred embodiment of the invention, X is halo and $X^1$ is hydrogen or halo.

Examples of compounds of the invention embraced by Formula I include:

2-chloro-4-trifluoromethyl-3'-W-chloropropoxycarbonyl-4'-nitrodiphenyl ether;

2,6-dichloro-4-trifluoromethyl-3'-trifluoroethoxycarbonyl-4'-nitrodiphenyl ether;

2-fluoro-4-trifluoromethyl-3'-(α-methyl-α-nitrobutoxycarbonyl-4'-nitrodiphenyl ether;

4-trifluoromethyl-3'-(β-methyl-β-cyanobutoxycarbonyl)-4'-nitrodiphenyl ether;

2-nitro-4-trifluoromethyl-3'-(β-phenethoxycarbonyl)-4'-nitrodiphenyl ether;

2-cyano-4-trifluoromethyl-3'-(β-methylthioethoxycarbonyl)-4'-nitrodiphenyl ether;

2-methyl-4-trifluoromethyl-3'-(ε-methylsulphonylpentoxycarbonyl)-4'-nitrodiphenyl ether);

2,4-bit(trifluoromethyl)-3'-(ε-acetoxybutoxycarbonyl)-4'-nitrodiphenyl ether;

2-chloro-4-trifluoromethyl-3'-(furfuryloxycarbonyl)-4'-nitrodiphenyl ether;

4-trifluoromethyl-3'-(4-pyridyl)methoxycarbonyl-4'-nitrodiphenyl ether;

2,6-difluoro-4-trifluoromethyl-3'-[2-3-pyrrollyl)ethoxycarbonyl]-4'-nitrodiphenyl ether;

2-chloro-4-trifluoromethyl-3'-(3-[2-pyrazinyl]-propoxycarbonyl)-4'-nitrodiphenyl ether;

2-chloro-4-trifluoromethyl-3'-[(2-thienyl)methoxycarbonyl]-4'-nitrodiphenyl ether;

2-chloro-4-trifluoromethyl-3'-[(3-thienyl))methoxycarbonyl]-4'-nitrodiphenylether;

2-chloro-4-trifluoromethyl-3'-[(2-thiazolyl)methoxycarbonyl]-4'-nitrodiphenylether;

2-chloro-4-trifluoromethyl-3'-[(4-thiazolyl)methoxycarbonyl]-4'-nitrodiphenylether;

2-chloro-4-trifluoromethyl-3'-[(5-thiazolyl)methoxycarbonyl]-4'-nitrodiphenylether;

2-chloro-4-trifluoromethyl-3'-[(2-oxazolyl)methoxycarbonyl]-4'-nitrodiphenylether;

2-chloro-4-trifluoromethyl-3'-[(4-oxazolyl)methoxycarbonyl[-4'-nitrodiphenylether;

2-chloro-4-trifluoromethyl-3'-[(5-oxazolyl)methoxycarbonyl]-4'-nitrodiphenylether;

2-chloro-4-trifluoromethyl-3'-[(2-(1,3,4-oxadiazolyl)methoxycarbonyl]-4'-nitrodiphenylether;

2-chloro-4-trifluoromethyl-3'-[(2-(1,3,4-thiadiazolyl)-methoxycarbonyl]-4'-nitrodiphenylether;

2-chloro-4-trifluoromethyl-3'-[(5-(1,2,3,4-tetrazolyl)methoxycarbonyl]-4'-nitrodiphenylether;

2-chloro-4-trifluoromethyl-3'-[(3-pyridazinyl)methoxycarbonyl]-4'-nitrodiphenylether;

2-chloro-4-trifluoromethyl-3'-[(4-pyridazinyl)methoxycarbonyl]-4'-nitrodiphenylether;

2-chloro-4-trifluoromethyl-3'-[(2-pyrimidinyl)methoxycarbonyl]-4'-nitrodiphenylether;

2-chloro-4-trifluoromethyl-3'-[(4-pyrimidinyl)methoxycarbonyl]-4'-nitrodiphenylether;

2-chloro-4-trifluoromethyl-3'-[(5-pyrimidinyl)methoxycarbonyl]-4'-nitrodiphenylether;

2-chloro-4-trifluoromethyl-3'-[(2-pyrazinyl)methoxycarbonyl]-4'-nitrodiphenylether;

2-chloro-4-trifluoromethyl-3'-[(2-tetrahydrofurfuryl)-methoxycarbonyl]-4;-nitrodiphenylether;

2-chloro-4-trifluoromethyl-3'-[(3-tetrahydrofurfuryl)-methoxycarbonyl]-4;-nitrodiphenylether;

2-chloro-4-trifluoromethyl-3'-[(2-tetrahydrothienyl)methoxycarbonyl]-4'-nitrodiphenylether;

2-chloro-4-trifluoromethyl-3'-[(3-tetrahydrothienyl)methoxycarbonyl]-4'-nitrodiphenylether;

2-chloro-4-trifluoromethyl-3'-[(2-acetoxy)ethoxycarbonyl]-4'-nitrodiphenylether; and 2-chloro-4-trifluoromethyl-3'-[3-(2-oxo)tetrahydrofurfuryloxycarbonyl]-4'-nitrodiphenylether.

The products of this invention may be prepared by one of two methods which comprises treating an acid halide with a hydroxy substituted compound or by treating an alkali metal or alkaline earth metal carboxylate with a halo substituted compound.

The first process comprises treating 4-trifluoromethylphenyl-3-halocarbonyl-4-nitrophenyl ether with an hydroxy compound in the presence of an inert solvent such as toluene and the like. The reaction may be conducted at a temperature in the range of from about 20 to about 150° C. for a period of time of from about 15 minutes to about 16 hours; however, the reaction is generally conducted at a temperature between 50 to 100° C. for a period of time of about 1/2 to about 2 hours. The following equation illustrates this process:

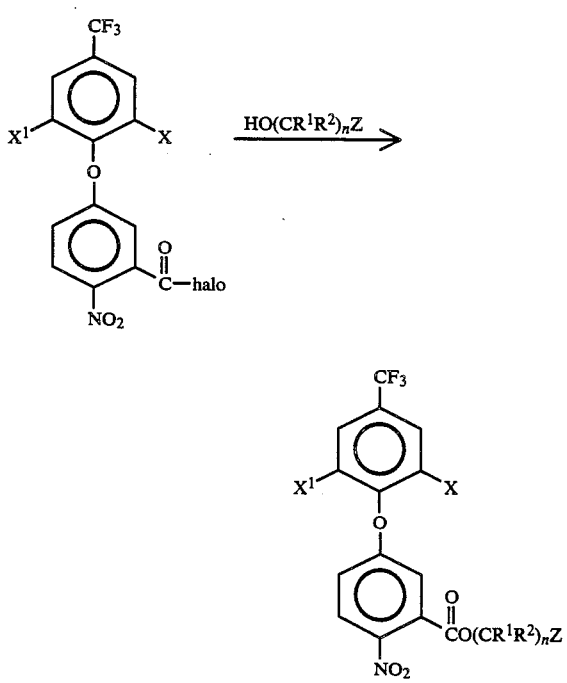

wherein X, $X^1$, $R^1$, $R^2$, n and Z are as defined above.

The second process comprises treating 4-trifluoromethylphenyl-3-alkali metal (or alkaline earth metal) oxycarbonyl-4-nitrophenyl ether with a halo substituted compound in the presence of an inert solvent such as dimethyl formamide, dimethyl sulfoxide, methyl ethyl ketone, and the like at a temperature in the range of from about 20 to about 150° C. for a period of time in the range of from about 1/4 to about 16 hours.

The following equation illustrates this process.

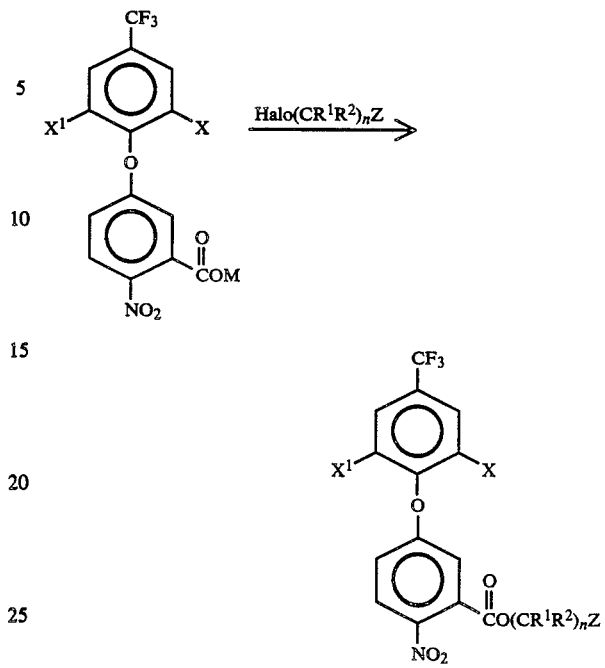

wherein X, $X^1$, $R^1$, $R^2$, n and Z are as defined above and M is a cation derived from an alkali metal.

The diphenyl ethers (I, supra) of the invention are useful as preemergence and postemergence herbicides. Preemergence herbicides are ordinarily used to treat the soil by application either before seeding, during seeding, after seeding and before the crop emerges. Postemergence herbicides are those which are applied after the plants have emerged and during their growth period. The compounds of this invention are especially active as postemergence herbicides.

Among the crops on which the diphenyl ethers of the invention can be advantageously employed are, cotton, soybeans, peanuts, beans, peas, carrots, corn, wheat, and other cereal crops.

The diphenyl ethers (I, supra) are useful for controlling weeds in rice crops. When used in transplanted rice crops, the ethers can be applied either preemergence or postemergence to the weeds -- that is, they can be applied to the transplanted rice plants and their growth medium either before the weed plants have emerged or while they are in the early stages of growth. The ethers can be applied to the growth medium either before or after the rice has been transplanted to that medium.

The diphenyl ethers (I, supra) can be applied in any amount which will give the required control of weeds. A standard rate of application of the herbicides of the invention is in the range from about 0.1 to about 12 pounds of diphenyl ether per acre. A preferred range is from about 0.1 to about 2 pounds per acre.

Under some conditions, the diphenyl ethers (I, supra) may be advantageously incorporated into the solid or other growth medium prior to planting a crop. This incorporation can be by any convenient means, including simple mixing with the soil, applying the diphenyl ether to the surface of the soil and then disking or dragging into the soil to the desired depth, or by employing a liquid carrier.

The diphenyl ethers of the invention can be applied to the growth medium or to plants to be treated either near or as a component in a herbicidal composition or formulation which also comprises an agronomically acceptable carrier. "Agronomically acceptable carrier" is any carrier which can be used to dissolve, disperse or diffuse a herbicidal compound in the composition without impairing the effectiveness of the herbicidal compound and which by itself has no permanent detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated. It is usually desirable, particularly in post-emergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

Examples of solvents which are useful in the practice of this invention include alcohols, ketones, aromatic hydrocarbons, dimethyl formamide, dioxane, dimethyl sulfoxide, and the like. Mixtures of these solvents can also be used. The concentration of the solution can vary from about 2% to about 98% of active product with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, and can be as high as about 75%.

Wettable powders suitable for spraying, can be prepared by admixing the compound with a finely divided solid, such as clays, inorganic silicates and carbonates and silicas and then incorporating wetting agents, sticking agents, and/or dispersing agents. The concentration of active ingredients in such formulations is usually in the range of about 20% to about 98%, and preferably about 40% to about 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to about 80% of the active ingredient are commonly made and are subsequently diluted to about 1% to about 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise from about 2 to about 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by method commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

CARBOXYLIC ACIDS AND SALTS AND ESTER DERIVATIVES THEREOF 2,3,6-trichlorobenzoic acid, 2,3,5,6-tetrachlorobenzoic acid, 2-methoxy-3,5,6-trichlorobenzoic acid, 2-methoxy-3,6-dichlorobenzoic acid, 2-methyl-3,6-dichlorobenzoic acid, 2,3-dichloro-6-methylbenzoic acid, 2,4-dichlorophenoxyacetic acid, 2,4,5-trichlorophenoxyacetic acid, 2-methyl-4-chlorophenoxyacetic acid, 2-(2,4,5-trichlorophenoxy)propionic acid, 4-(2,4-dichlorophenoxy)butyric acid, 4-(2-methyl-4-chlorophenoxy)butyric acid, 2,3,6-trichlorophenylacetic acid, 3,6-endoxohexahydrophthalic acid, dimethyl 2,3,5,6- tetrachloroterephthalate, trichloroacetic acid, 2,2,-dichloropropionic acid, 2.3-dichloroisobutyric acid,

CARBAMIC ACID DERIVATIVES ethyl N,N-di(n-propyl)thiocarbamate, propyl N,N-di-(n-propyl)thiocarbamate, ethyl N-ethyl-N-(n-butyl)-thiocarbamate, ethyl N-ethyl-N-(n-butyl)thiocarbamate, propyl N-ethyl-N-(n-butyl)thiocarbamate, 2-chloroallyl N,N-diethyldithiocarbamate, N-methyldithiocarbamic acid salts, ethyl 1-hexamethyleneiminecarbothiolate, isopropyl N-phenylcarbamate, isopropyl N-(m-chlorophenyl)carbamate, 4-chloro-2-butynyl N-(m-chlorophenyl)carbamate, methyl N-(3,4-dichlorophenyl)carbamate.

PHENOLS dinitro-o-(sec-butyl)phenol and its salts, pentachlorophenol and its salts,

SUBSTITUTED UREAS 3-(3,4-dichlorophenyl)-1,1-dimethylurea, 3-phenyl-1,1-dimethylurea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, dichloral urea,

SUBSTITUTED TRIAZINES 2-chloro-4,6-bis(ethylamino)-s-triazine, 2-chloro-4-ethylamino-6-isopropylamino-s-triazine, 2-chloro-4,6-bis(methoxypropylamino)-s-triazine, 2-methoxy-4,6-bis-(isopropylamino)-s-triazine, 2-chloro-4-ethylamino-6-(3-methoxypropylamino)-s-triazine, 2-methylmercapto-4,6-bis(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(ethylamino)-s-triazine, 2-methoxy-4-ethylamino-6-(isopropylamino-s-triazine, 2-methylmercapto-4-(2-methoxyethylamino)-6-isopropylamine-s-triazine,

DIPHENYL ETHER DERIVATIVES 2,4-dichloro-4'-nitrodiphenyl ether, 2,4,6-trichlorophenyl ether, 2,4-dichloro-6-fluoro-4'-nitrodiphenyl ether 2,-chloro-4-trifluoromethyl-3'-carboxy-4'-nitrodiphenyl ether and its salt and ester derivatives, 3-methyl-4'-nitrodiphenyl ether, 3,5-dimethyl-4'-nitrodiphenyl ether, 2,4'-dinitro-4-trifluoromethyl-diphenyl ethers, 2,4-dichloro-3'-methoxy4'-nitrodiphenyl ether,

ANILIDES

N-(3,4-dichlorophenyl)propionamide, N-(3,4-dichlorophenyl)methacrylamide, N-(3-chloro-4-methylphenyl)-2-methylpentanamide, N-(3,4-dichlorophenyl)trimethylacetamide, N-(3,4-dichlorophenyl)-α,α-dimethylvaleramide, N-isopropyl-N-phenyl-chloroacetamide, N-n-butoxymethyl-N-(2,6-diethylphenyl)chloroacetamide and N-n-methoxymethyl-N-(2,6-diethylphenyl)chloroacetamide,

URACILS 5-bromo-3-s-butyl-6-methyluracil, 5-bromo-3-cyclohexyl-1,6-dimethyluracil, 3-cyclohexyl-5,6-trimethyleneuracil, 5-bromo-3-isopropyl-6-methyluracil and 3-tert-butyl-5-chloro-6-methyluracil,

NITRILES 2,6-dichlorobenzonitrile, diphenylacetonitrile, 3,5-dibromo-4-hydroxybenzonitrile, and 3,5-diiodo-4-hydroxybenzonitrile,

OTHER ORGANIC HERBICIDES 2-chloro-N,N-diallylacetamide, N-(1,1-dimethyl-2-propynyl)-3,5-dichlorobenazmide, maleic hydrazide, 3-amino-1,2,4-triazole, monosodium methanearsonate, disodium methanearsonate, N,N-dimethyl-α,α-diphenyolacetamide, N,N-di(n-propyl)-2,6-dinitro-4-trifluoromethylaniline, N,N-di(n-propyl)-2,6-dinitro-4-methylaniline, N,N-di(n-propyl)-2,6-dinitro-4-methylsulfonylaniline, 0-(2,4-dichlorophenyl)-0-methyl-isopropylphosphoramidothiaote, 4-amino-3,5,6-trichloropicolinic acid, 2,3-dichloro-1,4-naphthoquinone, di-(methoxythiocarbonyl)disulfide, 3-isopropyl-1H-2,1,3-benzothiadiazine(4)3H-one-2,2,dioxide, 6,7-dihydro dipyridol[1,2-a:2',1'-c]pyrazidinium salts, 1,1'-dimethyl-4,4'-bipyridinium salts and 3,4,5,6-tetrahydro-3,5-dimethyl-2-thio-2H-1,315-thiadiazine.

When mixtures of herbicides are employed, the relative proportions which are used will depend upon the crop to be treated and the degree of selectivity in weed control desired.

The following examples illustrate the compounds of this invention, however, the scope of the invention is not to be limited by these specific examples.

EXAMPLE 1

2-Chloro-4-trifluoromethyl-3'-(2-chloroethoxycarbonyl)-4'-nitrodiphenyl ether

To a 1 necked flask equipped with a stirrer is added 2-chloro-4-trifluoromethyl-3'-chlorocarbonyl-4'-nitrophenyl ether (19.0 grams; 0.05 moles), 2-chloroethanol (40 grams; 0.5 moles) and toluene (100 ml.). The solution was heated at reflux overnight. A sample taken for gas liquid chromatography analysis indicated complete reaction. The solvent and excess 2-chloroethenol are removed on a rotorary evaporator to afford a gum which is dissolved in hexane and washed with dilute potassium carbonate solution and then water. The hexane solution is dried over magnesium sulfate then filtered through activated silica gel. The solvent was removed to afford 22 grams of 2-chloro-4-trifluoromethyl-3'-(2-chloroethoxycarbonyl)-4'-nitrodiphenyl ether, melting point 58°-61° C. Elemental Analysis for $C_{16}H_{10}Cl_2F_3N\ O_5$: Calculated: C, 45.30; H, 2.38; N, 3.30; Cl, 16.72; F, 13.44; Found: C, 45.18; H, 2.42; N, 3.19; Cl, 16.94; F, 12.76.

EXAMPLE 2

2-Chloro-4-trifluoromethyl-3'-(2-nitroethoxycarbonyl)-4'-nitrodiphenyl ether

A solution of 2-chloro-4-trifluoromethyl-3'-chlorocarbonyl-4'-nitrodiphenyl ether (19.0 grams; 0.05 moles) and 2-nitroethanol (9.0 grams; 0.1 mole) in toluene (100 ml) is refluxed overnight and the solvents removed under reduced pressure to afford 18 grams of 2-chloro-4-trifluoromethyl-3'-(2-nitroethoxycarbonyl)-4'-nitrodiphenyl ether. Elemental analysis for $C_{16}H_{10}ClF_3N_2O_7$; Calculated: C, 44.20; H, 2.32; N, 6.44; Cl, 8.15 and F, 13.11; Found: C, 44,56; H, 2.28; N, 6.50; Cl, 8.46; and F, 12.60.

EXAMPLE 3

2-Chloro-4-trifluoromethyl-3'-(2-pyridylmethoxycarbonyl)-4'-nitrodiphenyl ether A solution of 2-chloro-4-trifluoromethyl-3'-chlorocarbonyl-4'-nitrodiphenyl ether (19.0 grams; 0.05 mole) and 2-pyridylcarbinol (10.9 grams; 0.1 moles) in toluene (100 ml.) is refluxed overnight. The procedure of Example 1 is followed in working up the reaction mixture to obtain 22 grams of 2-chloro-4-trifluoromethyl-3'-(2-pyridylmethoxycarbonyl)-4'-nitrodiphenyl ether. Elemental analysis for $C_{20}H_{12}ClF_3N_2O_5$: Calculated: C, 52.93; H, 2.89; N, 6.17; Cl, 7.81; F, 12.56; Found: C, 52.57; H, 2.82; N, 6.16; Cl, 8.43; F, 11.97.

EXAMPLE 4

2-Chloro-4-trifluoromethyl-3'-(cyanomethoxycarbonyl-4'-nitrodiphenyl ether

2-Chloro-4-trifluoromethyl-3-carboxy-4'-nitrodiphenyl ether (18.05 grams; 0.05 moles) and potassium carbonate (anhydrous; 6.9 grams) in dimethylsulfoxide (100 ml.) is heated to 100° C. with stirring. The reaction mixture is cooled to 40° C. and chloroacetonitrile (4.0 grams) is added and the reaction mixture heated again to 100° C. with stirring. Stirring is continued for 2 hours and then the reaction mixture is cooled, diluted with water and extracted with diethyl ether. The extract is diluted with hexane and washed with 1% sodium hydroxide solution. The extract is dried, filtered through activated silica gel and the solvents removed under reduced pressure to afford 13.0 grams of 2-chloro-4-trifluoromethyl-3'-cyanomethoxycarbonyl-4'-nitrodiphenyl ether as a pale yellow oil. Elemental analysis for $C_{16}H_8N_2ClF_3O_5$: Calculated: C, 47.96; H, 2.01; N, 6.99; Cl, 8.85; F, 14.22; Found: C, 47.52; H, 1.82; N, 65.73; Cl, 8.75; F, 14.60.

EXAMPLE 5

2-Chloro-4-trifluoromethyl-3'(methylthiomethoxycarbonyl)-4'-nitrodiphenyl ether To a methylethyl ketone solution of 2-chloro-4-trifluoromethyl-3'-carboxy-4'-nitrodiphenyl ether (7.23 g, 0.20 mole) at 25° C. is added potassium carbonate (27.6 g, 0.20 mole). The mixture is heated to 60° C. for 10 minutes. Chloromethylmethylsulfide (19.3 g, 0.20 mole) is then added and the emulsion stirred 3 hours at 65.75° C. The emulsion is diluted with ether, washed with water, and aqueous potassium carbonate solution, dried with molecular sieves and filtered through activated silica gel. Removal of the solvent affords 2-chloro-4-trifluoromethyl-3'(methylthiomethoxycarbonyl)-4'-nitrodiphenyl ether as an oil (48.5 g, 58.5%), 90% pure by nmr. $^1$H n.m.r. of 3' side-chain (CDCl$_3$) 2.25 (s, 3H), 5.35 (s, 2H). IR (cm') 1725 (carbonyl), 700 (C-S). Elemental Analysis calculated for $C_{16}H_{11}ClF_3N_1O_5S_1$: Found: C, 45.71; H, 2.84; N, 3.04; Calculated: C, 45.55; H, 2.63; N, 3.32.

EXAMPLE 6

2-Chloro-4-trifluoromethyl-3'(methylsulfinylmethoxycarbonyl)-4'-nitrodiphenyl ether To a chloroform solution of 2-chloro-4-trifluoromethyl-3'(methylthiomethoxycarbonyl)-4'-nitrodiphenyl ether (10.5 g, 0.02 mole) at 25° C. is added a chloroform solution of m-chloroperoxybenzoic acid (4.06 g, 0.02 mole). The solution is stirred overnight at 25° C. and then for one hour under reflux. After cooling, the solution is washed with water, aqueous potassium carbonate and sodium sulfite, and dried by molecular sieves. After filtering through activated silica gel and stripping, an oily solid is obtained which was recrystallized from chloroform-hexane to afford 2-chloro-4-trifluoromethyl-3'(methylsulfinylmethoxycarbonyl)-4'-nitrodiphenyl ether white crystals (1.7 g, 19.3%) m.p. 130°–132° C., 90% pure by nmr. Elemental Analysis calculated for $C_{16}H_{11}Cl_1F_3N_1O_6S_1$: Found: C, 42.52; H, 2.58; N, 3.00; Calculated: C, 43.89; H, 2.53; N, 3.20.

EXAMPLE 7

2-Chloro-4-trifluoromethyl-3'-(methylsulfonylmethoxycarbonyl)-4'-nitrodiphenyl ether To a chloroform solution of 2-chloro-4-trifluoromethyl-3'(methylthiomethoxycarbonyl)-4'-nitrodiphenyl ether (9.6 g, 0.023 mole) at 25° C. is added a chloroform solution of m-chloroperoxybenzoic acid (18.5 g, 0.91 mole) and the solution stirred overnight at 25° C., then for 1 hour at 40° C. The solution is then washed with water, aqueous potassium carbonate and sodium sulfite solutions. After drying with molecular sieves, the solution is filtered through activated silica gel and stripped to afford 2-Chloro-4-trifluoromethyl-3'-(methylsulfonylmethoxycarbonyl)-4'-nitrodiphenyl ether as an oil (1.8 g, 17.3%, 74% by nmr. $^1$H n.m.r. of 3' side-chain (CDCl$_3$) 2.95 (s, 3H), 5.28 (s, 2H). IR (cm$^{-1}$) 1759 (carbonyl), 1125 and 1320 (SO$_2$). Elemental Analysis calculated for $C_{16}H_{11}Cl_1F_3N_1O_7S_1$: Found: C, 42.88; H, 2.62; N, 2.38; Calculated: C, 42.34; H, 2.44; N, 3.09.

EXAMPLE 8

2-Chloro-4-trifluoromethyl-3-[α-(acetyl)ethoxycarbonyl]4'-nitrodiphenyl ether To a methylethyl ketone solution of 2-chloro-4-trifluoromethyl-3'-carboxy-4'-nitrodiphenyl ether (14.5 g, 0.04 mole) at 25° C. is added potassium carbonate (11.04 g, 0.08 mole). The mixture is stirred for 20 minutes. To this mixture is then added a methylethyl ketone solution of 3-bromo-2-butanone (6.04 g, 0.04 mole) and stirred 3 hours at 25° C. The mixture is diluted with ether, washed with water and aqueous solutions of sulfuric acid and potassium carbonate. After drying with molecular sieves, the solution is filtered through activated silica gel and on removal of the solvent affords 2-chloro-4-trifluoromethyl-3-[(acetyl)ethoxycarbonyl]4'-nitrodiphenyl ether as an oil (14.1 g, 81.6%) 90% pure by nmr. $^1$H n.m.r. of 3'side-chain δ (CDCl$_{32}$) 1.58 (d, 3H), 2.28 (d, 3H), 5.38 (quart., 1H). IR (cm-1) 1740 (carbonyl). Elemental Analysis calculated for $C_{18}H_{13}Cl_1F_3N_1O_6$: Found: C, 48.55; H, 2.96; N, 3.23; Cl, 9.00; F, 12,52; Calculated: C, 50.07; H, 3.03; N, 3.24; Cl, 8.21; F, 13.20.

EXAMPLE 9

2-Chloro-4-trifluoromethyl-3'(furfuryloxycarbonyl)4-'nitrodiphenyl ether

To a refluxing toluene solution of 2-chloro-4-trifluoromethyl-3'-carboxy-4'-nitrodiphenyl ether (14.5 g, 0.04 mole) is added a toluene solution of furfuryl alcohol (4.5 g, 0.045 mole). The solution is heated at reflux for 10 hours. The mixture is diluted with hexane and washed with water and aqueous solutions of sodium carbonate and brine. The organic phase is then treated with activated carbon, dried with magnesium sulfate filtered first through activated silica gel and then through basic alumina. Removal of the solvent affords 2-chloro-4-trifluoromethyl-3'(furfuryloxycarbonyl)4'-nitrodiphenyl ether as an oil (4.7 g, 26.6%), 90% pure by nmr. $^1$H n.m.r. of 3' side-chain δ (CDCl$_3$) 5.38 (s, 1H), 6.3–6.58 (m, 6H). IR (cm$^{-1}$) 1740 (carbonyl). Elemental Analysis calculated for C$_{19}$H$_{11}$Cl$_1$F$_3$N$_1$O$_6$: Found: C, 53.13; H, 2.69; N, 2.98; Cl, 7.60; F, 10.85; Calculated: C, 51.65; H, 2.51; N, 3.17; Cl, 8.03; F, 12.90.

In a manner similar to that described in Examples 1 or 4 all of the diphenyl ethers of this invention may be obtained. Thus by substituting the appropriately substituted hydroxy compounds or halo compounds for the 2-nitroethanol or chloroacetonitrile of Examples 1 and 4 respectively, and by following substantially the procedures described in Examples 1 and 4 respectively, the diphenyl ether products of this invention may be obtained. The following equation illustrates the reaction of Examples 1 and 4 and taken together with table 1 depict the starting materials and products obtained thereby.

TABLE I

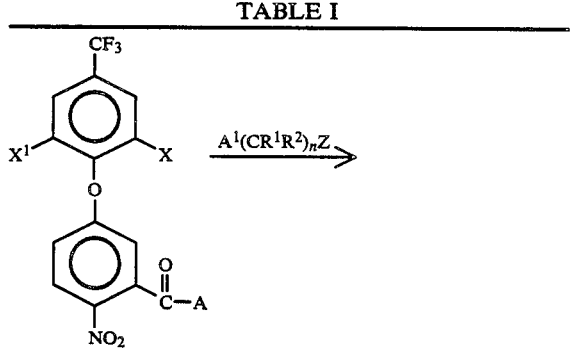

| Ex. No. | X | X$^1$ | A | A$^1$ | R$^1$ | R$^2$ | n | Z |
|---|---|---|---|---|---|---|---|---|
| 10 | Cl | Cl | Cl | OH | H | CH$_3$ | 2 | F |
| 11 | Cl | H | Cl | OH | H | H | 2 | Cl |
| 12 | CF$_3$ | H | ONa | Cl | H | H | 3 | ⟨tetrahydrofuranyl⟩ |
| 13 | CF$_3$ | H | ONa | Br | H | H | 4 | ⟨piperazinyl⟩ |
| 14 | CN | H | Cl | OH | CH$_3$ | CH$_3$ | 2 | ⟨pyridinyl⟩ |
| 15 | F | Br | ONa | Br | H | H | 5 | NO$_2$ |
| 16 | CH$_3$ | H | Cl | OH | CH$_3$ | CH$_3$ | 3 | ⟨thienyl-isopropyl⟩ |
| 17 | Cl | H | Cl | OH | H | H | 3 | CF$_3$ |

HERBICIDAL ACTIVITY

The following illustrates the herbicidal activity of the diphenyl ethers of this invention exhibited on the following representative species:

| | | | Approx. No. Seeds |
|---|---|---|---|
| Monocots | Barnyardgrass | (*Echinochloa crusgalli*) | 25 |
| | Downybrome | (*Bromus tectorum*) | 20 |
| | Foxtail | (*Setaria* spp) | 25 |
| | Johnsongrass | (*Sorghum halepense*) | 25 |
| | Nutsedge | (*Cyperus esculentus*) | 5 |
| | Wild Oat | (*Avena fatua*) | 20 |
| Dicots | Cocklebur | (*Xanthium pensylvanicum*) | 3 |
| | Marigold | (*Tagetes* spp) | 15 |
| | Morningglory | (*Ipomoea* spp) | 10 |
| | Tomato | (*Lycopersicon esculentum*) | 15 |
| | Velvetleaf | (*Abutilon theophrasti*) | 15 |

TEST PROCEDURE

Seeds of the above species are planted in soil in trays (approx. 7″×10−1/2″×3″). For preemergence tests, the trays are sprayed with the test compound immediately after planting. For postemergence tests, the seeds are allowed to germinate and after growing in the greenhouse for two weeks, the growing plants are treated with the test compound. The compound to be evaluated is dissolved in acetone or water and sprayed over the trays using a carrier volume equivalent to 50 gallons per acre at the rate of application (in pounds per acre, lb/A) specified in the table. About two weeks after application of the test compound, the state of growth of the plants is observed and the phytotoxic effect of each compound determined as follows: each species is evaluated on a scale of 0–100 in which 0 = no activity and 100 = total kill and the results for the monocots and dicots separately averaged. The following table shows the results obtained for the compounds of the invention at 0.5 lg/A. and 2.0 lb/A.

| | 0.5 lb/A | | | | 2.0 lb/A | | | |
|---|---|---|---|---|---|---|---|---|
| | Pre | | Post | | Pre | | Post | |
| Example No. | AM 1/ | AD 2/ | AM | AD | AM | AD | AM | AD |
| 1 | — | — | — | — | 76 | 97 | 43 | 66 |
| 2 | — | — | — | — | 81 | 92 | 30 | 97 |
| 3 | — | — | — | — | 52 | 64 | 23 | 70 |
| 4 | 72 | 72 | 18 | 80 | 94 | 99 | 42 | 99 |
| 5 | 45 | 96 | 32 | 80 | 77 | 93 | 53 | 100 |
| 6 | 52 | 84 | 18 | 100 | 77 | 99 | 47 | 100 |
| 7 | 43 | 80 | 20 | 80 | 33 | 72 | 30 | 78 |
| 8 | 38 | 56 | 5 | 52 | 53 | 98 | 20 | 86 |
| 9 | 55 | 99 | 30 | 76 | 87 | 98 | 47 | 86 |

One skilled in the art will appreciate that the above examples are merely illustrative and are capable of a wide variation and modification without departing from

What is claimed is:

1. A compound of the formula

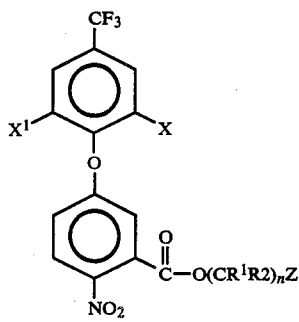

wherein X is hydrogen, halo, trihalomethyl, alkyl, cyano, or nitro; $X^1$ is hydrogen, halo or trifluoromethyl; $R^1$ and $R^2$ are the same or different radicals selected from hydrogen, lower alkyl, phenyl or benzyl; n is an integer of from 1 to 5; and Z is nitro.

2. The compound of claim 1 wherein X is hydrogen, chloro, trifluoromethyl, methyl or cyano; $X^1$ is hydrogen, chloro or trifluoromethyl; $R^1$ and $R^2$ are the same or different radicals selected from hydrogen or methyl; n is an integer of from 1 to 5 and Z is nitro.

3. The compound of clam 2 names 2-chloro-4-trifluoromethyl-3'-(2-nitroethoxycarbonyl)-4'-nitrodiphenyl ether.

4. A herbicidal composition comprising the compound of claim 1 and an agronomically acceptable carrier.

5. A herbicidal composition comprising the compound of claim 2 and an agronomically acceptable carrier.

6. A herbicidal composition comprising the compound of claim 3 and an agronomically acceptable carrier.

7. A method for controlling weeds which comprises applying an effective amount of the compound of claim 1.

8. A method for controlling weeds which comprises applying an effective amount of the compound of claim 2.

9. A method for controlling weeds which comprises applying an effective amount of the compound of claim 3.

10. The method of claim 7 wherein the composition is applied preemergent.

11. A method of claim 7 wherein the composition is applied postemergent.

* * * * *